(12) United States Patent
Hakonarson et al.

(10) Patent No.: US 6,893,828 B2
(45) Date of Patent: May 17, 2005

(54) METHODS FOR PRODUCING EX VIVO MODELS FOR INFLAMMATORY DISEASE AND USES THEREOF

(75) Inventors: Hakon Hakonarson, Reykjavik (IS); Michael M. Grunstein, Merion, PA (US)

(73) Assignees: deCODE genetics ehf., Reykjavik (IS); The Children's Hospital of Philadelphia, Philadelphia, PA (US)

(*) Notice: Subject to any disclaimer, the term of this patent is extended or adjusted under 35 U.S.C. 154(b) by 154 days.

(21) Appl. No.: 09/947,954

(22) Filed: Sep. 6, 2001

(65) Prior Publication Data

US 2003/0049598 A1 Mar. 13, 2003

(51) Int. Cl.$^7$ .................. G01N 33/53; G01N 33/567

(52) U.S. Cl. .................. 435/7.21; 435/7.1; 435/7.2; 435/7.24

(58) Field of Search .................. 435/7.21, 7.1, 435/7.2, 7.24

(56) References Cited

U.S. PATENT DOCUMENTS

| | | |
|---|---|---|
| 2003/0113831 A1 | 6/2003 | Hakonarson |
| 2003/0134776 A1 | 7/2003 | Hakonarson |

FOREIGN PATENT DOCUMENTS

| | | |
|---|---|---|
| WO | WO02/059367 A2 | 8/2002 |
| WO | WO 03/021261 A3 | 3/2003 |

OTHER PUBLICATIONS

Heller et al. Proc. Natl. Acad. Sci. USA vol. 94, pp. 2150–2155, 1997.*
Ortaldo et al. (2001), The Journal of Immunology, 166: 4994–4999.*
Clarke, P., et al., "Gene Expression Profiling of Human Colon Cancer Cells Following Inhibition of Signal Transduction by 17–Allylamino–17–Demethoxygeldanamycin, an Inhibitor of the hsp90 Molecular Chaperone," *Oncogene*, 19:4125–4133 (2000).
Galon, J., et al., "Gene Profiling Reveals Unknown Enhancing and Suppressive Actions of Glucocorticoids on Immune Cells," *FASEB Journal*, 16:61–71 (2002).
Heller R., et al., "Discovery and Analysis of Inflammatory Disease–Related Genes Using cDNA Microarrays," *Proc. Natl. Acad. Sci. USA*, 94:2150–2155 (1997).
Heyninck, K., et al., "The Cytokine–Inducible Zinc Finger Protein A20 Inhibits IL–1 Induced NF–κB Activation at the Level of TRAF6," *FEBS*, 442:147–150 (1999).
Khoo, C., et al., "Differential Expression of Cysteine–rich Intestinal Protein in Liver and Intestine in $CCl_4$–Induced Inflammation," *American Physiological Society*, 270:G613–G618 (1996).

Saban, M., et al., "Time Course of LPS–Induced Gene Expression in a Mouse Model of Genitourinary Inflammation," *Physiol. Genomics*, 5:147–160 (2001).
Sutherland, A., "Gene Expression Analysis in Immunmodulatory and Inflammatory Model Systems Using Affymetrix Genechip Expression Arrays," *Cell Biology International*, 24:975 (2000).
Eggleston, P. and Bush, R., "Environmental allergen avoidance: An Overview," *J. Allergy Clin. Immunol.* 107:S403–5 (2001).
"Genes for Asthma? An Analysis of The European Community Respiratory Health Survey," *Am. J. Respir. Crit. Care Med.* 156:1773–1780 (1997).
Golub, T., et al., "Molecular Classification of Cancer: Class Discovery and Class Prediction by Gene Expression Monitoring," *Science* 286: 531–537 (1999).
Gulcher, J. and Stefansson, K., "Population Genomics: Laying the Groundwork for Genetic Disease Modeling and Targeting," *Clin. Chem. Lab. Med.* 36: 523–527 (1998).
Grunstein M. et al. "Autocrine signaling by IL–10 mediates altered resonsiveness of atopic sensitized airway smooth muscle," *Am. J. Physiol. Lung Cell. Mol. Physiol.* 281: L1130–7 (2001).
Hakonarson, H. et al. "Autocrine Role of Interleukin 1β in Altered Responsiveness of Atopic Asthmatic Sensitized Airway Smooth Muscle," *J. Clin. Invest.* 99: 117–124 (1997).
Hakonarson, H. et al. "Mechanism of Rhinovirus–induced Changes in Airway Smooth Muscle Responsiveness," *J. Clin. Invest.* 102: 1732–1741 (1998).
Hakonarson, H. et al. "Autocrine interaction between Il–5 and IL–1β mediates altered responsiveness of atopic asthmatic sensitized airway smooth muscle," *J. Clin. Invest.* 104: 657–667 (1999).
Hakonarson, H. et al. "Association between Il–1beta/TNF–alpha Induced Glucocorticoid–Sensitive Changes in Multiple Gene Expression and Altered Responsiveness in Airway Smooth Muscle," *Am. J. Respir. Cell Mol. Biol.* 25: 761–71 (2001).
Leung, D. and Chrousos, G., "Is There a Role for Glucocorticoid Receptor Beta in Glucocorticoid–dependent Asthmatics," *Am. J. Respir. Crit. Care Med.* 162: 1–3 (2000).

(Continued)

*Primary Examiner*—Prema Mertz
(74) *Attorney, Agent, or Firm*—Hamilton, Brook, Smith & Reynolds, P.C.

(57) ABSTRACT

The present invention relates to methods for inducing a pro-asthma/pro-inflammatory like state in a resident tissue cell, comprising contacting the cell with IL-1β, TNFα or both. Methods are also disclosed for identifying genes that regulate responses to anti-inflammatory drugs, to methods for drug screening, and to methods for identifying genes that correlate with various pro-asthma/pro-inflammatory disease phenotypes.

4 Claims, 9 Drawing Sheets

OTHER PUBLICATIONS

Keller, A., et al., "Bayesian classification of DNA array expression data," Technical report, Department of Computer Science and Engineering, University of Washington (Aug. 2000).

Arend, W., "Physiology of Cytokine Pathways in Rheumatoid Arthritis," *Arthritis Care and Research* 45:101–106 (2001).

Barnes, P. et al., "Efficacy and Safety of Inhaled Corticosteroids," *Am. J. Respir. Crit. Care. Med.* 157:S1–S53 (1998).

Broide, D. et al., "Cytokines in Symptomatic Asthma Airways," *J. Allergy Clin. Immunol.* 89:958–967 (1992).

* cited by examiner

METHODS FOR PRODUCING EX VIVO MODELS FOR INFLAMMATORY DISEASE AND USES THEREOF

GOVERNMENT SUPPORT

The invention was supported by grants HL-59906, HL-31467, HL-58245 and HL-61038 from the National Heart, Lung and Blood Institute. The Government has certain rights in the invention.

BACKGROUND OF THE INVENTION

The pleiotropic cytokines, IL-1β and TNFα, among other effectors, have been implicated in the pathophysiology of asthma and other inflammatory diseases. Altered airway responsiveness to bronchoactive constrictor and relaxant stimuli is the characteristic pathophysiological feature of bronchial asthma. While infiltration of the airways with inflammatory cells, principally involving eosinophils, mast cells, and lymphocytes is characteristic of altered airway responsiveness, airway smooth muscle (ASM) itself has the capacity to autologously induce changes in its constrictor and relaxant responsiveness secondary to the induced release and autocrine actions of certain pro-inflammatory cytokines. For example, IgE-dependent atopic sensitization and rhinovirus inoculation of ASM provoke the release of Th1- and Th2-type cytokines, IL-1β, and other cytokines from the ASM itself, and these cytokines acting alone or in combination elicit changes in ASM responsiveness.

Effectors such as cytokines typically are involved in a broad class of signaling events. Indeed, altered levels in IL-1β and TNFα signaling activity are observed in inflammatory diseases other than asthma as well.

SUMMARY OF THE INVENTION

The present invention relates to methods for determining a patient's responsiveness to treatment for asthma or related inflammatory conditions.

In one embodiment, the invention is directed to a method for inducing a pro-inflammatory like state in a resident tissue cell, comprising contacting the cell with a cytokine that induces a pro-inflammatory like state such as, for example, IL-1β, TNFα or both. Cells induced to exhibit a pro-inflammatory like state can be, for example, airway smooth muscle cell, epithelial cell, keratinocyte, synovial cell, glial cell and villous intestinal cell. The pro-inflammatory like state can be a pro-asthma like state.

In another embodiment, the invention is directed to a resident tissue cell induced to exhibit a pro-inflammatory like state according to the methods described herein. Resident tissue cells can be, for example, airway smooth muscle or airway epithelial cells.

In another embodiment, the invention is directed to a method for screening drug candidates for treating an inflammatory disease, including: contacting a resident cell induced to exhibit a pro-inflammatory like state according to the methods described herein with a drug candidate for treating the inflammatory disease; and assaying for a pro-inflammatory like state, such that an absence of the pro-inflammatory like state is indicative of the drug candidate being effective in treating the inflammatory disease. In a particular embodiment, the inflammatory disease can be asthma, atopy, rheumatoid arthritis, psoriasis, inflammatory bowel disease (IBD) and chronic obstructive pulmonary disease (COPD). Atopy can be rhinitis, conjunctivitis, dermatitis and eczema.

In another embodiment, the invention is directed to a method for screening drug candidates for treating an inflammatory disease, including: contacting a resident tissue cell induced to exhibit a pro-inflammatory like state according to the methods described herein with a drug candidate for treating an inflammatory disease; and assaying for a pro-inflammatory like state, such that an absence of the pro-inflammatory like state is indicative of the drug candidate being effective in treating an inflammatory disease. In a particular embodiment, the inflammatory disease can be asthma, atopy, rheumatoid arthritis, psoriasis, IBD and COPD.

In another embodiment, the invention is directed to a method of identifying genes associated with an inflammatory disease, including: obtaining resident tissue cells induced to mimic the inflammatory disease; assaying the expression level of at least one gene in the cells; comparing the expression level to the baseline expression levels in cells not induced to mimic the inflammatory disease; and identifying a difference in expression level in cells induced to mimic the inflammatory disease versus cells that do not mimic the inflammatory disease, such difference indicating the gene is associated with the inflammatory disease. In another embodiment, the invention is directed to a method for identifying genes that are involved in regulating drug responses and present candidate genes for development of new therapy for treating an inflammatory disease, including: contacting a cell induced to exhibit a pro-inflammatory like state according to the methods described herein with a drug candidate for treating the inflammatory disease; and assaying for a pro-inflammatory like state, such that genes whose expression correlates with an absence of the pro-inflammatory like state are indicative of the gene being involved with regulating the response to the drug in treating the inflammatory disease. In one embodiment, the inflammatory disease can be asthma, atopy (e.g., rhinitis, conjunctivitis, dermatitis or eczema), rheumatoid arthritis, psoriasis, IBD or COPD. In one embodiment, the informative gene can be selected from the genes described in Tables 1 and 2.

In yet another embodiment, the invention is directed to a method for diagnosing an inflammatory disease, including: obtaining or generating a gene expression profile from a sample for at least one informative gene identified by methods described herein; comparing the expression profile of the informative gene to a reference expression profile for the informative gene in a cell induced for pro-asthma/pro-inflammatory like conditions; and comparing the expression profile of the informative gene to a reference expression profile for the informative gene in a cell that does not exhibit pro-asthma/pro-inflammatory like conditions, wherein similarity between the sample expression profile of the informative gene and either of the reference expression profiles allows for a positive or negative diagnosis of the patient from whom the sample was obtained. In one embodiment, the informative gene can be selected from the genes described in Tables 1 and 2.

In yet another embodiment, the invention is directed to an expression profile indicative of the presence of asthma in a patient, including at least one informative gene of Table 1 and Table 2.

BRIEF DESCRIPTION OF THE DRAWINGS

The foregoing and other objects, features and advantages of the invention will be apparent from the following more particular description of preferred embodiments of the invention, as illustrated in the accompanying drawings.

DETAILED DESCRIPTION OF THE INVENTION

A description of preferred embodiments of the invention follows.

The present invention is directed to methods for inducing cells to exhibit pro-inflammatory like characteristics, to methods for drug screening, to methods for identifying genes that are differentially expressed in cells displaying pro-inflammatory like characteristics versus normal cells, and to the genes thus identified. The invention is based upon the discovery that cultured cells can be induced to mimic a pro-inflammatory like state. The methods disclosed herein, in part, refer to the activation of the IL-1β/TNFα signaling pathway, the activation of which is shared among inflammatory diseases in addition to asthma. Hence, as used herein, "pro-asthma" like characteristics refer to "pro-inflammatory" like characteristics in particular cells affected by asthma. As used herein, "pro-inflammatory like" is a description of a state or characteristics associated with inflammatory diseases in general with asthma being a well characterized and well studied example of inflammatory diseases. Thus, pro-asthma like characteristics are also pro-inflammatory like characteristics and, where referred to herein, are meant to describe characteristics caused by differential levels of effectors specific to inflammatory disease. The term is not limiting to conditions associated specifically with asthma. However, as asthma is a well characterized example of inflammatory disease, characteristics associated with asthma are also common for other inflammatory diseases.

Asthma, or Reversible Obstructive Airway Disease (ROAD), is a condition in which the airways of the lungs become either narrowed or completely blocked, impeding normal breathing and leading to potentially more severe health problems. Although normal airways have the potential for constricting in response to allergens or irritants, the asthmatic's airways are oversensitive or hyper-reactive. In response to stimuli, the airways may become obstructed by one of the following: constriction of the muscles surrounding the airway; inflammation and swelling of the airway; or increased mucus production which clogs the airway. Once the airways have become obstructed, it takes more effort to force air through them, so that breathing becomes labored. Because exhaling through the obstructed airways is difficult, too much stale air remains in the lungs after each breath. This accumulation of stale air decreases the amount of fresh air that can be taken in with each new breath, so not only is there less oxygen available for the whole body, the high concentration of carbon dioxide in the lungs causes the blood supply to become acidic as well. This acidity in the blood may rise to toxic levels if the asthma remains untreated.

Although asthma creates difficulties in breathing and can lead to more serious problems, the lung obstruction associated with asthma is reversible, either spontaneously or with medication. Asthmatics can take anti-inflammatory agents such as corticosteroids, brochodilators and leukotriene antagonists reduce inflammation and asthma symptoms. Although asthma has been treated by these methods for several years, a significant fraction of asthma patients are resistant to treatment. As there are risks associated with methods for treating asthma, identification of patients that will be responsive to treatment is important. Methods described herein are used to identify genes that regulate drug response. Described herein are methods for inducing conditions in cultured cells that mimic asthma and inflammatory disease conditions and methods for utilizing said cultured cells in methods for diagnosing disease, drug screening and obtaining expression profiles.

Corticosteroids are sometimes also referred to as "steroids." This type of medication is not related to the anabolic steroids that are misused by some athletes to increase performance. Rather, corticosteroids have been used as a treatment for asthma and allergies since 1948. They decrease airway inflammation and swelling in the bronchial tubes; reduce mucus production by the cells lining the bronchial tubes; decrease the chain of overreaction (hyper-reactivity) in the airways; and assist the airway smooth muscle to respond to other medications such as beta-agonist drugs. Corticosteroids can be administered in a variety of ways, such as through the use of an inhaler, topically, orally, or through injection. Topical preparations (on specific surface areas such as skin or the lining of the bronchial tubes) may be applied as creams or sprays (inhalers). Corticosteroid inhalers are recommended for patients with daily, moderate or severe asthma symptoms. Oral corticosteroids and injected corticosteroids are generally only prescribed for those with severe asthma symptoms.

Although the use of corticosteroids has been commonplace for several years, they are not always effective and significant side effects do occur. Some people experience minor side effects of hoarseness and thrush (a fungal infection of the mouth and throat) from using corticosteroid inhalers. Also, long-term use of inhaled corticosteroids has been implicated in reduced growth velocity in children. Oral corticosteroids can have more side effects than inhaled corticosteroids. Oral corticosteroids are prescribed for long durations only when other treatments have failed to restore normal lung function and the risks of uncontrolled asthma are greater than the side effects of the steroids. For example, prednisone, one of the most commonly prescribed corticosteroids, can lead to possible side effects of weight gain, increased appetite, menstrual irregularities and cramps, heartburn, and indigestion. Some patients experience side effects such as loss of energy, poor appetite, and severe muscle aches or joint pains when their dosage of cortisone tablets is decreased. Long-term oral corticosteroid use may cause side effects such as ulcers, weight gain, cataracts, weakened bones and skin, high blood pressure, elevated blood sugar, easy bruising and decreased growth in children. Such side effects indicate a need to accurately assess the efficacy of corticosteroid treatment in asthmatic patients.

Bronchodilators, also called "β2-agonists", are non-steroidal anti-inflammatory medications often used as short-term "rescue" medications to immediately relieve asthma symptoms. Bronchodilators include albuterol, bitolterol, pirbuterol and terbutaline. Additionally, salmeterol is a long-acting β2-agonist that is intended to be used on a long-term basis, along with an anti-inflammatory medication, for controlling asthma. Those using salmeterol should take the medication on a daily basis, even if they are feeling fine, as it prevents symptoms. Although sporadically effective, bronchodilators are not typically useful in cases of severe asthma.

Many of the cells involved in causing airway inflammation are known to produce signaling molecules within the body called "leukotrienes." Leukotrienes are responsible for causing the contraction of the airway smooth muscle, increasing leakage of fluid from blood vessels in the lung, and further promoting inflammation by attracting other inflammatory cells into the airways. Oral anti-leukotriene medications have been introduced to fight the inflammatory response typical of allergic disease. These drugs are used in the treatment of chronic asthma. Recent data demonstrates that prescribed anti-leukotriene medications can be beneficial for many patients with asthma, however, a significant number of patients do not respond to anti-leukotriene drugs.

The present invention relates, in part, to methods for inducing a pro-inflammatory like state in cultured cells. In a preferred embodiment, this involves increasing the level of particular pro-asthma like effectors (e.g., cytokines such as, for example, IL-1β and TNFα). Pro-asthma like characteristics include, for example, heightened constrictor responsiveness to cholinergic stimulation and impaired relaxation to β-adrenergic receptor stimulation ans airway inflammation. Accordingly, airway smooth muscle ("ASM") contractility in the presence of acetylcholine ("ACh"), and impaired ASM relaxation in response to isoproterenol, for example, can be taken as examples of pro-asthma and, thereby, pro-inflammatory like characteristics. Characteristics further include those that are exhibited in asthmatic patients or patients with an inflammatory disease. Such characteristics can be used to determine the pro-asthma/pro-inflammatory like state. An assay for a subset or all known characteristics can be used to determine a pro-asthma/pro-inflammatory like state in resident tissue samples and cultured cells.

While infiltration of the airways with inflammatory cells, principally involving eosinophils, mast cells, and lymphocytes, is implicated in the etiology of the altered airway responsiveness, recent studies have determined that, under specific conditions, the airway smooth muscle (ASM) itself has the capacity to autologously induce changes in its constrictor and relaxant responsiveness secondary to the induced release and autocrine actions of certain pro-inflammatory cytokines. Comparable autologous mechanisms have also been shown to exist in various epithelial cells, keratinocytes, synovial cells, glial cells and villous intestinal cells. The present invention relates, in part, to methods for inducing a pro-inflammatory (e.g., pro-asthma like state) like state in resident tissue samples and cultured cells. Such cells can be, for example ASM cells, epithelial cells, keratinocytes, synovial cells, glial cells and villous intestinal cells.

A pro-asthma like phenotype is associated with, for example, elevated levels of at least one effector such as certain cytokines, including tumor necrosis factor alpha (hereinafter, "TNFα") and interleukin 1-beta (hereinafter, "IL-1β"). These cytokines are also elevated patients with other inflammatory diseases, and, thus, cells induced to mimic a pro-asthma/pro-inflammatory like state can be used to model, ex vivo, inflammatory disease generally (including, but not limited to, asthma, atopy (e.g., rhinitis, conjunctivitis, dermatitis, eczema), rheumatoid arthritis, psoriasis, IBD and COPD). As other effectors (e.g., cytokines, signaling molecules, chemical and physical stimuli) are characterized, the methods described herein can be used in conjunction with additional effectors to induce the pro-asthma like state. In a preferred embodiment, the invention relates, in part, to methods for elevating the cellular level of TNFα and IL-1β, thereby inducing asthma-like or comparable changes in the responsiveness of the cells. Such cells, since they can be taken as a model for inflammatory disease, can be used in screening for drugs, screening for informative genes, and obtaining expression profiles for genes indicative of asthma and other inflammatory diseases. It should be understood that any cytokine that induces a pro-inflammatory like state by exerting an inductive effect on TNFα and IL-1β expression and activity can be used as alternatives to or in combination with TNFα and/or IL-1β.

The cellular levels of TNFα and IL-1β can be increased by a variety of methods known in the art. For example, mammalian cells, such as ASM cells, epithelial cells, keratinocytes, synovial cells, glial cells and villous intestinal cells grown in culture can be exposed to isolated and purified TNFα and IL-1β such that these cytokines are taken up by the cells (typically, exposure of about 4 hours of TNFα at a concentration of 5 ng/mL and IL-1β at a concentration of 1 ng/mL in culture will produce pro-asthma/pro-inflammatory like symptoms in cultured cells. Other methods for expression of cytokines in cells grown in culture, e.g., by transfection of genes cloned into expression vectors, or by contacting cells with effectors that are known to induce particular cytokines, are known in the art, and would allow for a similar induction of pro-asthma/pro-inflammatory or pro-inflammatory like conditions in cells.

The present invention also relates to methods for determining genes that regulate responses to anti-inflammatory drugs, e.g., corticosteroids, used to treat inflammatory diseases such as asthma. The particular genes, herein referred to as "informative genes," are identified in cells that have been induced to mimic asthma or other inflammatory conditions. A subset or all informative genes can be assayed for gene expression in order to generate an "expression profile" that includes genes that regulate drug responses. As used herein, an "expression profile" refers to the level or amount of gene expression of one or more informative genes in a given sample of cells at one or more time points. A "reference" expression profile is a profile of a particular set of informative genes under particular conditions such that the expression profile is characteristic of a particular condition. As used herein, "gene" is a term used to describe a genetic element that gives rise to expression products (e.g., pre-mRNA, mRNA, and polypeptides). For example, a reference expression profile that quantitatively describes the expression of the informative genes listed in Tables 1 and 2 can be used as a reference expression profile for drug treatment and used to identify genes that regulate drug responses. Thus by comparing gene expression from a cell or tissue samples exposed to certain anti-inflammatory drugs with these reference expression profiles, genes that regulate drug responses can be identified.

The generation of an expression profile requires both a method for quantitating the expression from informative genes and a determination of the informative genes to be screened. The present invention describes screening changes in individuals that affect the expression levels of gene products in cells. As used herein, "gene products" are transcription or translation products that are derived from a specific gene locus. The "gene locus" includes coding sequences as well as regulatory, flanking and intron sequences. Expression profiles are descriptive of the level of gene products that result from informative genes present in cells. Methods are currently available to one of skill in the art to quickly determine the expression level of several gene products from a sample of cells. For example, short oligonucleotides complementary to mRNA products of several thousand genes can be chemically attached to a solid support, e.g., a "gene chip," to create a "microarray." Specific examples of gene chips include Hu95GeneFL (Affymetrix, Santa Clara, Calif.) and the 6800 human DNA gene chip (Affymetrix, Santa Clara, Calif.). Such microarrays can be used to determine the relative amount of mRNA molecules that can hybridize to the microarrays (Affymetrix, Santa Clara, Calif.). This hybridization assay allows for a rapid determination of gene expression in a cell sample. Alternatively, methods are known to one of skill in the art for a variety of immunoassays to detect protein gene expression products. Such methods can rely, for example, on conjugated antibodies specific for gene products of particular informative genes. Described herein are methods for identifying genes that regulate responses to inflammatory drugs used to treat inflammatory diseases. In an attempt to further elucidate those genes that may contribute to pro-asthmatic changes in ASM responsiveness, the effects of glucocorticoid treatment on ASM responsiveness and its associated pattern of altered gene expression in ASM cells exposed to IL-1β and TNFα can be examined. Glucocorticoids ameliorate asthma symptoms and altered responsiveness in asthmatic airways, as well as the ability of glucocorticoids to generally attenuate the expression of pro-inflammatory genes.

The identification of informative genes can be performed or verified under ex vivo conditions. For example, pro-inflammatory like conditions can be inducibly established in cultured cells. Described herein are methods, for example, for producing cells with pro-inflammatory like characteristics. Such cells can be used to obtain reference expression profiles. In one embodiment of the present invention, cells induced to exhibit pro-inflammatory like characteristics are used to first identify informative genes that exhibit altered gene expression in response to anti-inflammatory drugs in diseases such as, for example, asthma. Expression profiles can be obtained for induced cells that have been exposed to particular therapeutic agents (e.g., glucocorticoids such as dexamethasone or methylprednisolon), thus enabling identification of genes that are involved in regulating drug response.

IL-1β- and TNFα-related pathologies or diseases, as would be mimicked by the pro-inflammatory like state induced in the cells described herein, include, but are not limited to, inflammatory diseases or disorders, infections, neurodegenerative diseases, malignant pathologies, cachectic syndromes and certain forms of hepatitis.

Inflammatory diseases or disorders, include, but are not limited to, acute and chronic immune and autoimmune pathologies, such as, but not limited to, rheumatoid arthritis (RA), juvenile chronic arthritis (JCA), psoriasis, graft versus host disease (GVHD), scleroderma, diabetes mellitus, allergy; asthma, acute or chronic immune disease associated with an allogenic transplantation, such as, but not limited to, renal transplantation, cardiac transplantation, bone marrow transplantation, liver transplantation, pancreatic transplantation, small intestine transplantation, lung transplantation and skin transplantation; chronic inflammatory pathologies such as, but not limited to, sarcoidosis, chronic inflammatory bowel disease, ulcerative colitis, and Crohn's pathology or disease; vascular inflammatory pathologies, such as, but not limited to, disseminated intravascular coagulation, atherosclerosis, Kawasaki's pathology and vasculitis syndromes, such as, but not limited to, polyarteritis nodosa, Wegener's granulomatosis, Henoch-Schönlein purpura, giant cell arthritis and microscopic vasculitis of the kidneys; chronic active hepatitis; Sjögren's syndrome; psoriatic arthritis; enteropathic arthritis; reactive arthritis and arthritis associated with inflammatory bowel disease; and uveitis.

Infections include, but are not limited to, sepsis syndrome, cachexia (e.g., TNFα-mediated effects), circulatory collapse and shock resulting from acute or chronic bacterial infection, acute and chronic parasitic and/or infectious diseases, bacterial, viral or fungal, such as a human immunodeficiency virus (HIV), acquired immunodeficiency syndrome (AIDS) (including symptoms of cachexia, autoimmune disorders, AIDS dementia complex and infections).

Neurodegenerative diseases include, but are not limited to, demyelinating diseases, such as multiple sclerosis and acute transverse myelitis.

Malignant pathologies are associated with TNFα-secreting tumors or other malignancies involving TNFα, such as, for example, leukemias (acute, chronic myelocytic, chronic lymphocytic and/or myelodyspastic syndrome) and lymphomas (Hodgkin's and non-Hodgkin's lymphomas, such as malignant lymphomas (Burkitt's lymphoma or Mycosis fungoides)).

Cachectic syndromes and other pathologies and diseases involving excess TNFα, include, but not limited to, cachexia of cancer, parasitic disease and heart failure.

Elevated levels of TNFα are also associated with certain types of hepatitis, including, but not limited to, alcohol-induced hepatitis and other forms of chronic hepatitis.

One of skill in the art will recognize that reagents necessary to utilize certain methods described herein can be contained in a kit. Such reagents as described are either commercially available (e.g., buffered solutions, chemical reagents) or produced by methods known in the art (e.g., oligonucleotides, antibodies, ligands for detection). Thus, one of skill in the art would recognize that a kit can be produced containing in appropriate compartments, for example, all reagents, probes, and materials necessary for to allow for the practice of the methods described herein.

The invention will be further described with reference to the following non-limiting examples. The teachings of all the patents, patent applications and all other publications and websites cited herein are incorporated by reference in their entirety.

Exemplification

EXAMPLE 1

Ex vivo Model for Pro-inflammatory Like State

Elevated levels of the pleiotropic cytokines, IL-1β and TNFα, have been implicated in the pathophysiology of asthma and other inflammatory disorders (Broide, D. et al., 1992. *J. Allergy Clin. Immunol.* 89:958–967; Arend, W., 2001. *Arthritis Rheum.* 45:101–106). To elucidate the role of the cytokines IL-1β and TNFα in contributing to the pro-asthma like state, the effects of these cytokines on airway smooth muscle (ASM) responsiveness and ASM multiple gene expression, assessed by high-density oligonucleotide array analysis, were examined in the absence and presence of the glucocorticoid, dexamethasone (DEX).

In brief, administration of IL-1β/TNFα elicited increased ASM contractility to acetylcholine (ACh) and impaired ASM relaxation to isoproterenol. These pro-asthmatic like changes in ASM responsiveness were associated with IL-1β/TNFα induced upregulated mRNA expression of a host of pro-inflammatory genes that regulate gene transcription, cytokines and chemokines, cellular adhesion molecules, and various signal transduction molecules that regulate ASM responsiveness. In the presence of DEX, the induced changes in ASM responsiveness were abrogated, and most of the IL-1β/TNFα mediated changes in pro-inflammatory gene expression were repressed (Table 1), although mRNA expression of a small number of genes was further enhanced by DEX (Table 2). Collectively, the observations supports the novel concept that, together with its role as a regulator of airway tone, in response to IL-1β/TNFα, ASM expresses a host of glucocorticoid-sensitive genes that contribute to the altered structure and function of airways in the pro-asthmatic state. The glucocorticoid-sensitive, cytokine-induced gene pathways involved in ASM cell signaling represent important potential targets for new therapeutic interventions.

Animals

Ten adult New Zealand White rabbits were used in this study which was approved by the Biosafety and Animal Research Committee of the Joseph Stokes Research Institute at Children's Hospital of Philadelphia. The animals had no signs of respiratory disease prior to this study.

Preparation of ASM Tissues

After anesthesia with xylazine (10 mg/kg) and ketamine (50 mg/kg), the animals were sacrificed with systemic air embolism. The tracheas were removed via open thoracotomy, cleared of loose connective tissue, divided into eight ring segments of 6-8 mm in length, and incubated for 18 hr at room temperature in Dulbecco's modified Eagle's medium containing both IL-1β (10 ng/mL) and TNFα (100 ng/mL), or in medium alone with no added cytokines, both conditions in the absence and presence of dexamethazone (DEX;$10^{-5}$M). The medium was aerated with a continuous supplemental $O_2$ mixture (95% $O_2$/5% $CO_2$) during the incubation phase.

Pharmacodynamic Studies

After incubation, each airway segment was suspended longitudinally between stainless steel triangular supports in siliconized 20-mL organ baths (Harvard Apparatus, Inc., South Natick, Mass.). The lower support was secured to the base of the organ bath, and the upper support was attached via a gold chain to a force transducer (FT.03C; Grass Instrument Co., Quincy, Mass.) from which isometric tension was continuously displayed on a multichannel recorder. Care was taken to place the membranous portion of the trachea between the supports to maximize the recorded tension generated by the contracting trachealis muscle. The tissues were bathed in modified Krebs-Ringer solution containing (in mM) 125 NaCl, 14 $NaHCO_3$, 4 KCl, 2.25 $CaCl_2.2H_2O$, 1.46 $MgSO_4.7H_2O$, 1.2 $NaH_2PO4.H_2O$, and 11 glucose. The baths were aerated with 5% $CO_2$ in oxygen (a pH of 7.35–7.40 was maintained, and the temperature was held at 37° C.). Passive resting tension of each tracheal smooth muscle segment was set at 2.0 g after each tissue had been passively stretched to a tension of 8 g to optimize the resting length of each segment. The tissues were allowed to equilibrate in the bath for 45 minutes, at which time each tissue was primed with a 1 minute exposure to $10^{-4}$M acetylcholine (ACh). Cholinergic contractility was initially assessed in the ASM by cumulative administration of ACh in final bath concentrations from $10^{-9}$ to $10^{-3}$M. Thereafter, following thorough rinsing, each tissue segment was half-maximally contracted with ACh, and relaxation dose-response relationships to cumulative administration of isoproterenol ($10^{-9}$ to $10^{-4}$M) were generated in paired IL-1β/TNFα treated and control tissues in the absence and presence of co-treatment with DEX. The initial constrictor dose-response curves to ACh were analyzed in terms of the tissues' maximal isometric contractile force ($T_{max}$) and sensitivity to the agonist, expressed as the negative logarithm of the concentration of ACh producing 50% of $T_{max}$ ($pD_{50}$; i.e., geometric mean $ED_{50}$ value). The relaxant responses to isoproterenol were analyzed in terms of percent maximal relaxation ($T_{max}$) from the active cholinergic contraction, and sensitivity to the relaxing agent was determined as the corresponding $pD_{50}$ value associated with 50% $R_{max}$.

Description of Microarray Gene Expression Studies

Simultaneous multiple gene mRNA expression was examined in human ASM cells with the Affymetrix expression microarray system using human gene chips (HU95GeneFL array; Affymetrix, Santa Clara, Calif.) representing approximately 6000 genes. The ASM cells were derived from a 21 year old male donor (Clonetics Corp., San Diego, Calif.) who had no evidence of pulmonary disease, and the cells were carefully characterized by the manufacturer with specific markers to confirm their selective smooth muscle phenotype and to exclude contamination with other cell types. The cells were maintained at 37° C. in a humidified atmosphere of 5% $CO_2$/95% air and grown in a mixture of 5% Smooth muscle Basal Medium (SmBM), which was supplemented with 10% FBS, insulin (5 ng/mL), EGF (10 ng/mL; human recombinant), FGF (2 ng/mL; human recombinant), gentamycin (50 ng/mL), and amphotericin-B (50 ng/mL). Once the cells reached ~95% confluency, they were exposed for 4 hours to IL-1β (1 ng/mL) and TNFα (5 ng/mL) combined, or to media alone in the absence and presence of 1 hour pretreatment with DEX ($10^{-5}$M).

Following incubation of the cells, the total RNA used for the Affymetrix microarray expression analysis was extracted and purified using commercially available reagents and in accordance with methods recommended by the manufacturer (Affymetrix, Santa Clara, Calif.). Briefly, total RNA was extracted using Trizol and purified with Qiagen RNAEASY spin columns (Qiagen GmbH$_2$, Germany). Approximately 5 μg of RNA was used for first and second strand cDNA synthesis. After precipitation, the cDNAs were transcribed to cRNAs. The biotinylated cRNA was subsequently hybridized to the Affymetrix gene chips overnight. Non-bound probes were removed by stringency washing. The hybridized chips were developed using a Streptavidin-Phycoerythrin complex and scanned. The scanned images were then analyzed with Affymetrix software and the data was examined using commercially available software programs, including Spotfire Net 5.1 (Spotfire Inc, Mass.).

Description of the Effects of IL-1β and TNFα on ASM Responsiveness

Figure 1:
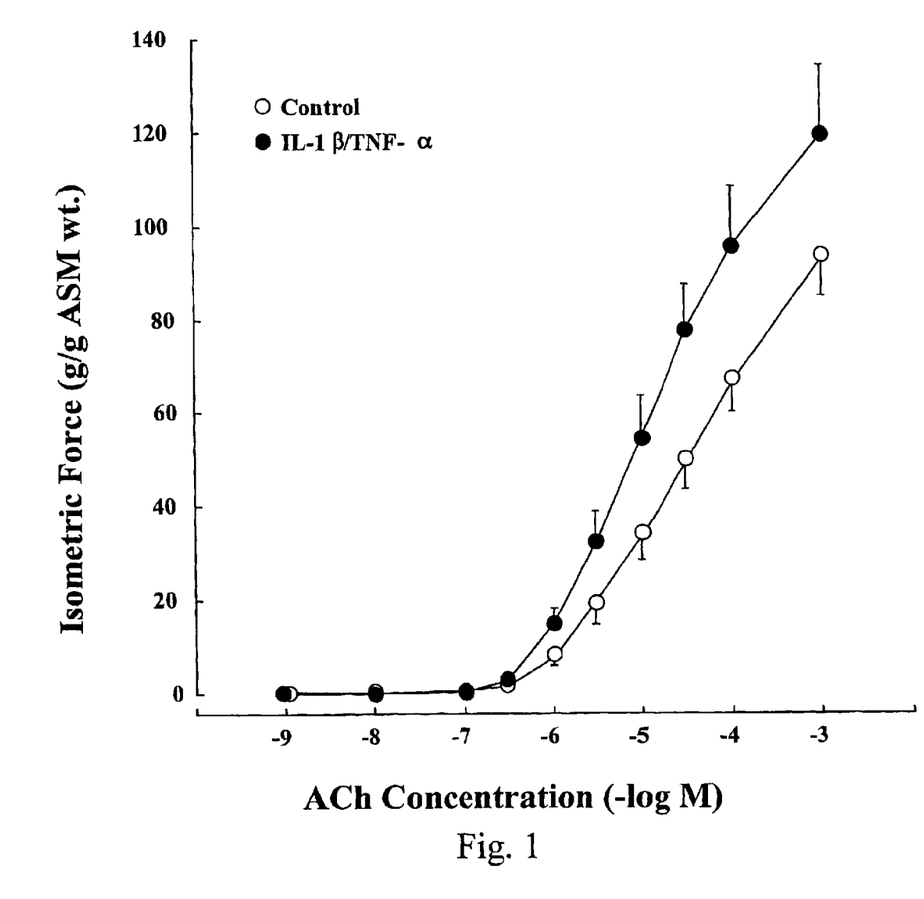
FIG. 1 is a graphical comparison of ASM constrictor responses to acetylcholine (ACh) in control (open symbols) and IL-1β/TNFα treated (filled symbols) ASM tissues. Data represent means ±SE from six paired experiments. Relative to tissues incubated with media alone, both $T_{max}$ and $ED_{50}$ responses to ACh were significantly enhanced (p<0.01 and <0.05, respectively) in ASM tissues that were co-incubated with IL-1β/TNFα, combined (filled symbols).

ASM constrictor dose-response relationships to ACh were determined in ASM tissues pre-incubated for 24 hours in medium alone and in the presence of maximally effective concentrations of IL-1β and TNFα. As shown in FIG. 1, relative to controls, the IL-1β/TNFα treated tissues exhibited significantly increased constrictor responsiveness to ACh, with mean ±SE values for maximal isometric force of contraction ($T_{max}$) amounting to 119.4±14.5 g/g ASM weight in the IL1β/TNFα treated ASM but 93.7±8.9 in the control ASM ($p<0.01$). Additionally, constrictor sensitivity to ACh was also relatively enhanced in the cytokine-treated tissues, with mean ±SE values for $pD_{50}$ (i.e.,-log $ED_{50}$) amounting to 4.95±0.06 -logM in the IL-1β/TNFα treated ASM but 4.66±0.12 in the control ASM ($p<0.05$).

Figure 2:
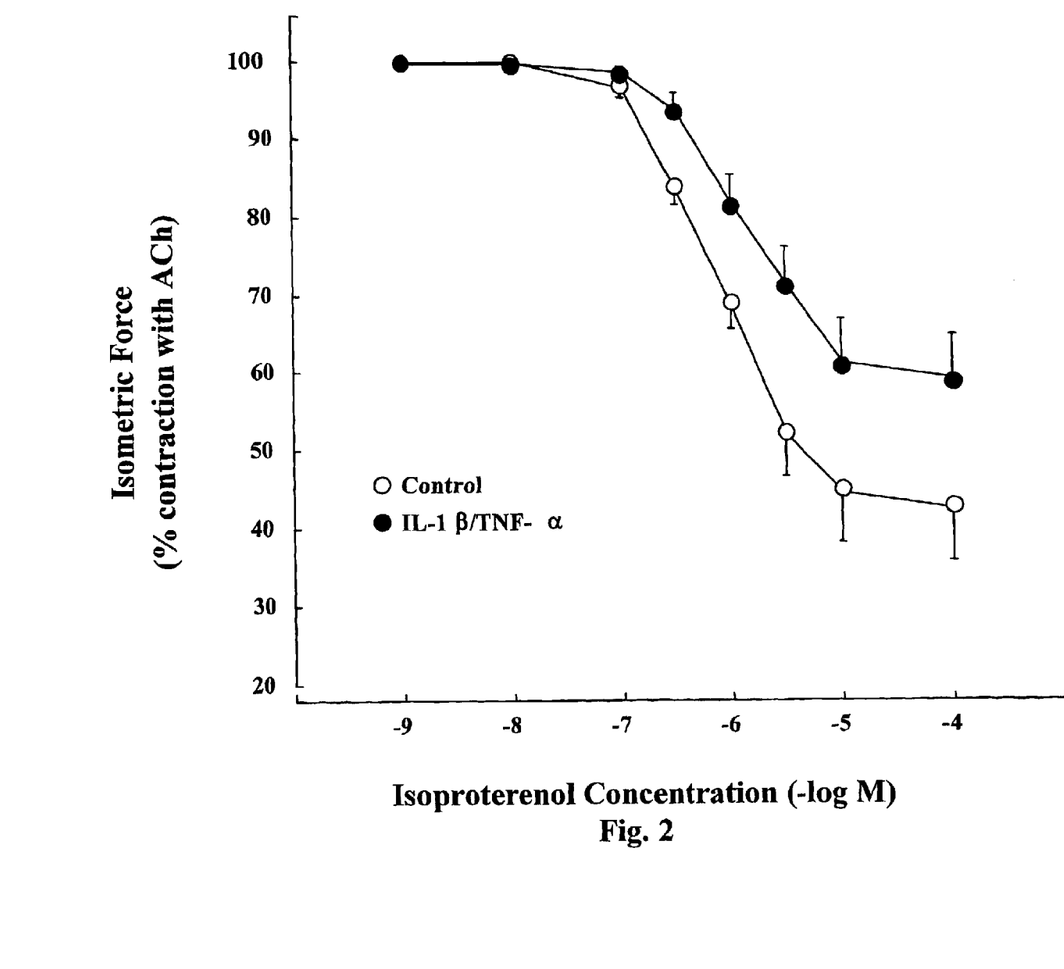
FIG. 2 is a graphical comparison of airway relaxant responses to isoproterenol in control (open symbols) and IL-1β/TNFα treated (filled symbols) ASM tissues. Data represent means ±SE from six paired experiments. Relative to tissues incubated with media alone, both $R_{max}$ and $pD_{50}$ responses to isoproterenol were significantly attenuated (p<0.01 and <0.05, respectively) in ASM tissues that were treated with IL-1β/TNFα, combined (filled symbols).

In separate studies, during comparable levels of initial sustained ACh-induced contractions, averaging ~50% of $T_{max}$, ASM relaxation responses to cumulative administration of the beta-adrenergic agonist, isoproterenol, were generated in control and IL-1β/TNFα treated tissues. As shown in FIG. 2, relative to controls, the maximal relaxation ($R_{max}$) responses and $pD_{50}$ values for isoproterenol were significantly attenuated in the IL-1β/TNFα treated tissues. Accordingly, the $R_{max}$ values amounted to 41.3±6.0 in the cytokine-treated ASM and 57.7±7.1% in the control ASM ($p<0.01$), and the corresponding $pD_{50}$ values amounted to 5.87±0.05 and 6.09±0.11 -logM, respectively ($p<0.05$).

Description of the Effects of IL-1β/TNFα on ASM Cell Gene Expression

In light of the above observations, to elucidate potential gene pathways associated with IL-1β/TNFα induced changes in ASM responsiveness, the effects of these cytokines on mRNA expression of multiple genes putatively involved in various cell signaling processes in ASM were examined in cultured human ASM cells. Accordingly, using a high density oligonucleotide DNA microarray analysis, in 4 separate experiments, it was determined that ~40% of genes were expressed in untreated ASM cells, and that treatment of cells with IL-1β/TNFα did not significantly alter the total number of genes expressed. More than 400 genes, however, demonstrated up- or down-regulation of their mRNA signals in response to IL-1β/TNFα administration. Given the established sensitivity of the expression technique applied, a two-fold increase in signal intensities from baseline was considered significant. Accordingly, ~70 genes that play a potential role in cell signaling in ASM demonstrated ≧2-fold (i.e., 2 to ~150-fold) increase in mRNA expression in response to IL-1β/TNFα. The latter collection of genes is categorically displayed in FIGS. 3–6, with the genes in each category identified by their symbols and GenBank accession number, and plotted in relation to their respective magnitudes (mean ±SE values of fold-increase) of altered mRNA expression.

Figure 3:
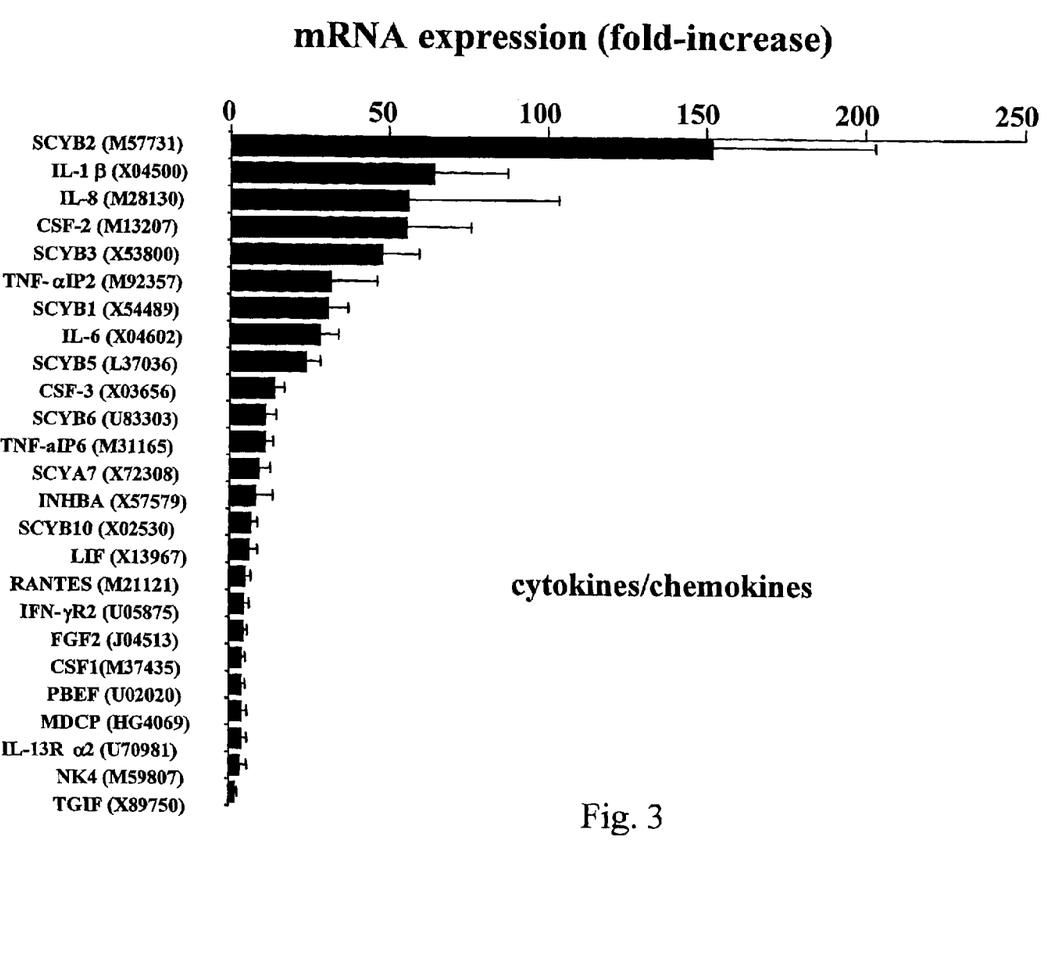
FIG. 3 is a graph showing ASM mRNA expression of 25 cytokine/chemokine genes demonstrating >2-fold change in expression following 4 hr exposure to IL-1β/TNFα combined, using gene array technology representing approximately 5000 genes. Each gene is identified by its gene symbol and GenBank accession number, and plotted in relation to its respective magnitude (mean ±SE values) of fold-change in expression from baseline values.
Figure 4:
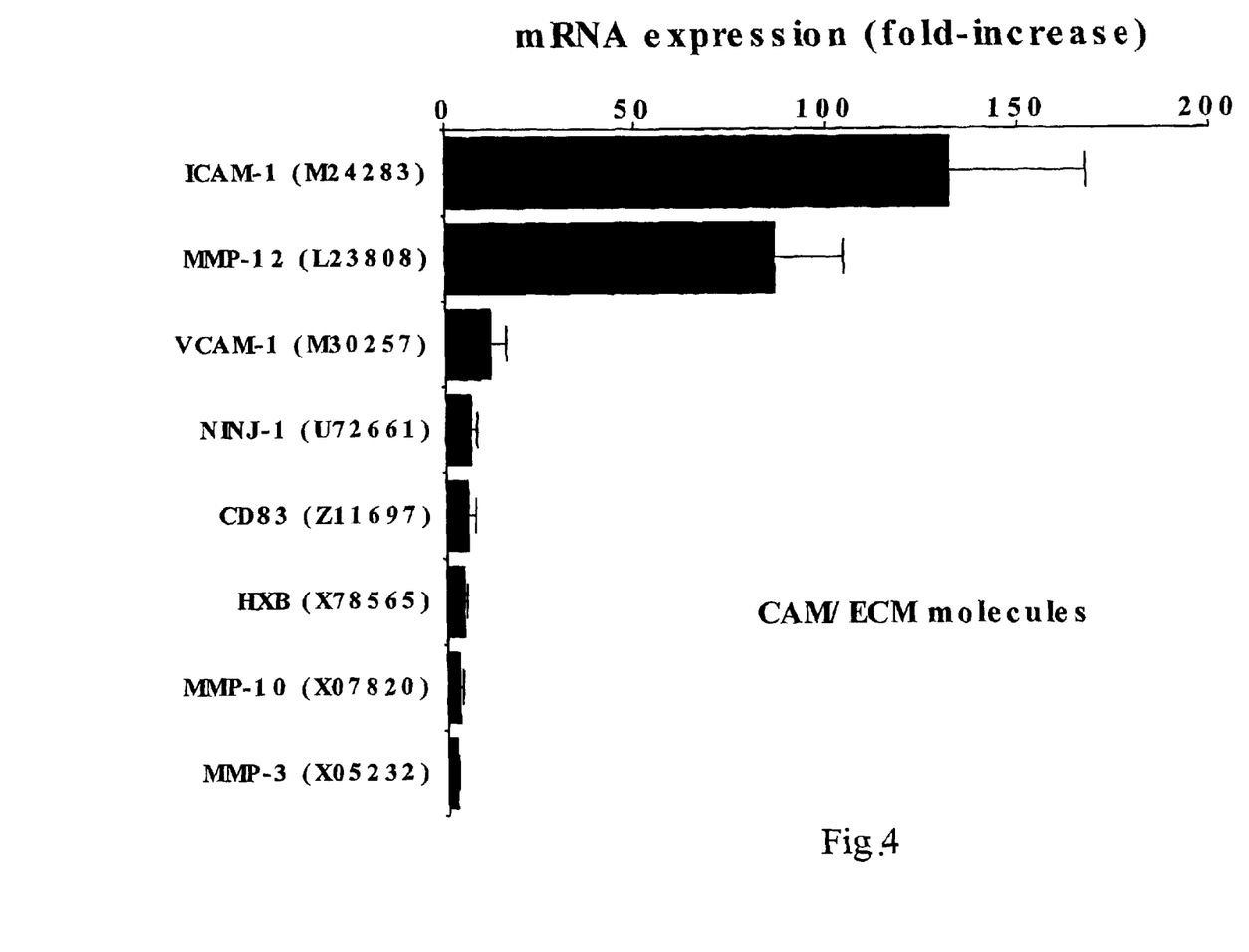
FIG. 4 is a graph showing ASM mRNA expression of 8 cell adhesion/extracellular matrix genes demonstrating >2-fold change in expression following 4 hr exposure to IL-1β/TNFα combined, using the Hu95GeneFL array from Affymetrix. Each gene is identified by its gene symbol and GenBank accession number, and plotted in relation to its respective magnitude (mean ±SE values) of fold-change in expression from baseline values.
Figure 5:
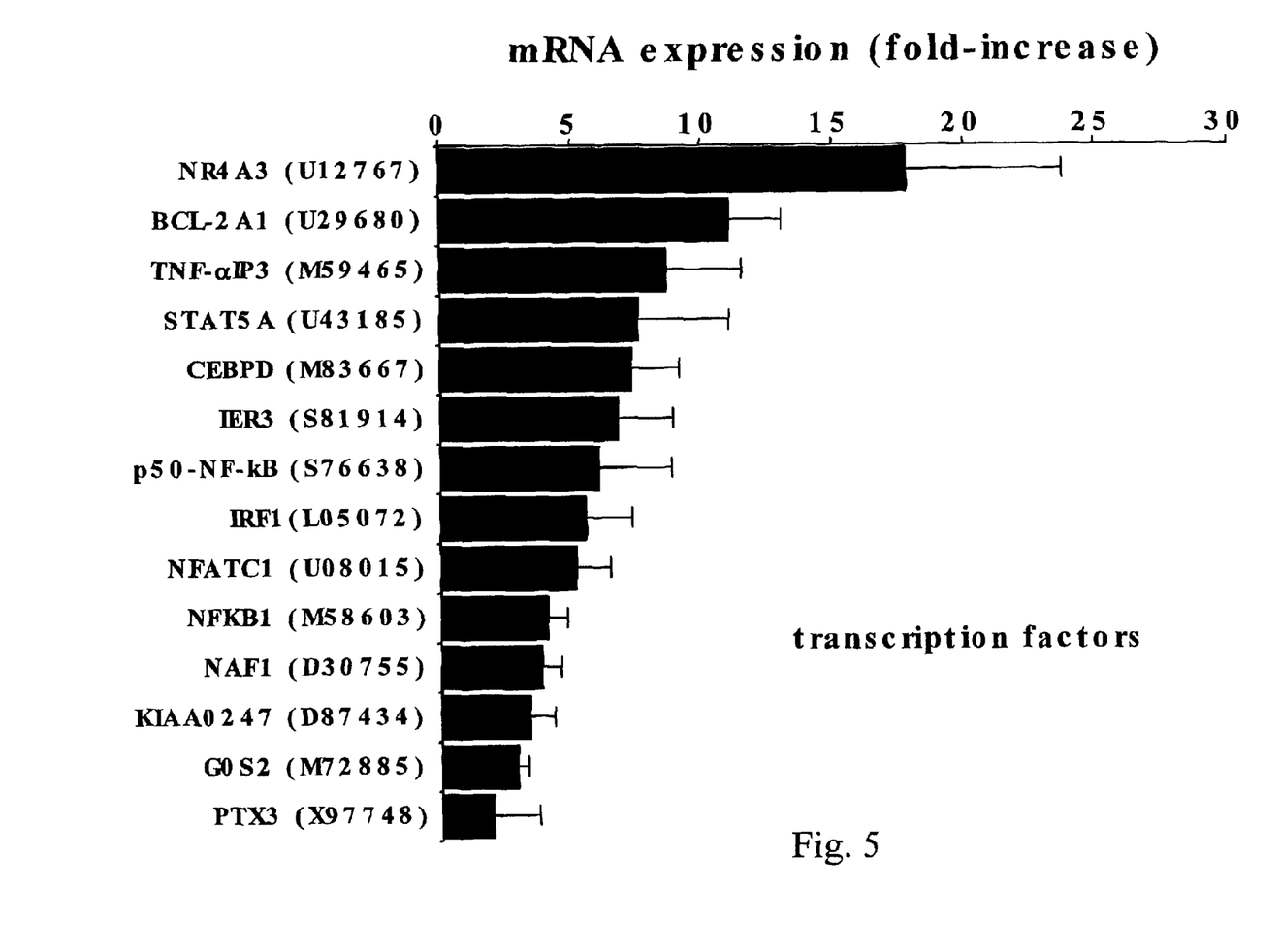
FIG. 5 is a graph showing ASM mRNA expression of 14 transcription factor genes demonstrating >2-fold change in expression following 4 hr exposure to IL-1β/TNFα combined, using the Hu95GeneFL array. Each gene is identified by its gene symbol and GenBank accession number, and plotted in relation to its respective magnitude (mean ±SE values) of fold-change in expression from baseline values.
Figure 6:
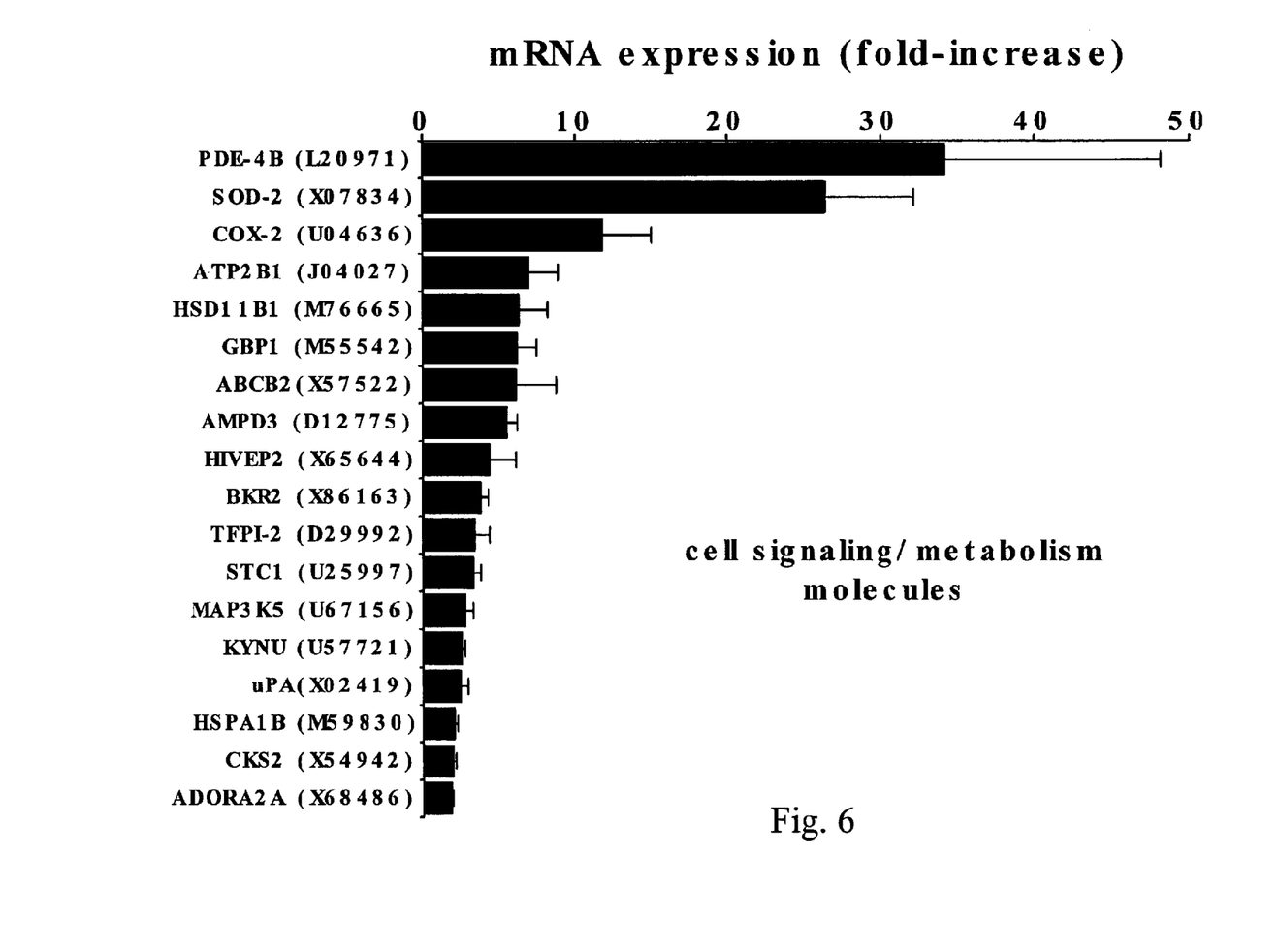
FIG. 6 is a graph showing ASM mRNA expression of 18 cell signaling/metabolism-related genes demonstrating >2-fold change in expression following 4 hr exposure to IL-1α combined, using the Hu95GeneFL array. Each gene is identified by its gene symbol and GenBank accession number, and plotted in relation to its respective magnitude (mean ±SE values) of fold-change in expression from baseline values.

Within the cytokine/chemokine category of genes, those depicting upregulated mRNA expression by an average of ≧10-fold above baseline in response to IL-1β/TNFα included the small inducible cytokine sub-family B (SCYB) members -2, -3, -1, -5, and -6, IL-1β, IL-8, CSF-2 (i.e., GM-CSF), TNFα-IP3, IL-6, and CSF-3 (FIG. 3). Within the cellular adhesion molecule (CAM)/extracellular matrix (ECM)-related category of genes, those upregulated ≧10-fold included ICAM-1, matrix metalloproteinase (MMP)-12, and VCAM-1 (FIG. 4), and, within the category of transcription factors, the genes comparably upregulated included NR4A3 and BCL-2A1 (FIG. 5). Other genes related to various aspects of cellular signaling/metabolism, including those encoding various proteases, kinases, and other molecules involved in signal transduction, were also upregulated in ASM cells in response IL-1β/TNFα administration (FIG. 6), most notably including phosphodiesterase 4B (PDE-4B), superoxide dismutase 2 (SOD-2), and inducible cyclooxygenase 2 (COX-2). Contrasting these observations, treatment of cells with IL-1β/TNFα had no effect on mRNA expression of constitutively expressed "house-keeping" genes such as β-actin, ribosomal protein L7, β2-microglobulin, and others.

Figure 7:
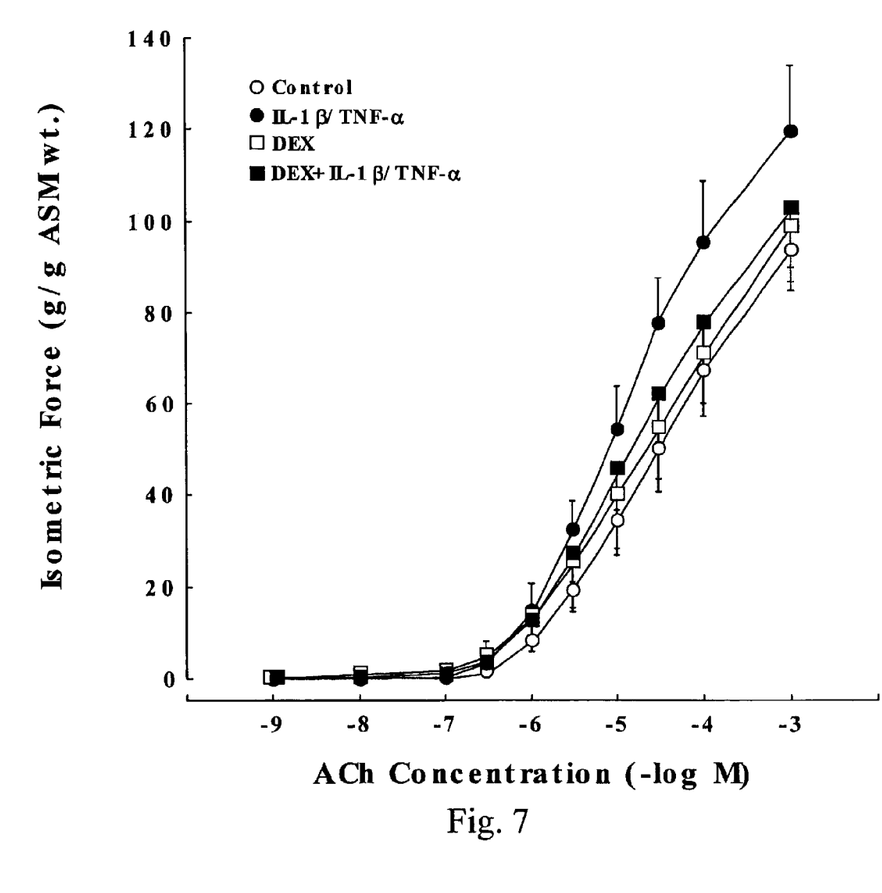
FIG. 7 is a graphical comparison of ASM constrictor responses to ACh in control (open circles) and IL-1β/TNFα treated ASM tissues in the absence (filled circles) and presence (filled squares) of pretreatment with dexamethasone $10^{-5}$M. Data represent means ±SE from six paired experiments. Relative to tissues incubated with media alone, both the $T_{max}$ and $ED_{50}$ responses to ACh were significantly enhanced in ASM segments that were exposed to IL-1β/TNFα, whereas the latter effects on the $T_{max}$ and $ED_{50}$ values were largely prevented by pre-treating the ASM tissues with dexamethasone (p≦0.01 and p≦0.05, respectively). In contrast, treatment with dexamethasone $10^{-5}$M alone (open squares), had no effects on either the $T_{max}$ or $ED_{50}$ responses to ACh.

Description of the Effects of Glucocorticoids on IL-1β/TNFα Induced Changes in ASM Responsiveness To assess whether the IL-1β/TNFα induced changes in ASM responsiveness are glucocorticoid-sensitive, contractile dose-response relationships to ACh were compared between IL-1β/TNFα treated ASM tissues and their respective paired control ASM segments, both in the absence and presence of pretreatment of the tissues for 1 hour with dexamethasone (DEX; $10^{-5}$M). As shown in FIG. 7, the heightened constrictor responses to ACh generated in IL-1β/TNFα exposed ASM were abrogated by pre-treating the cytokine-exposed tissues with DEX. Accordingly, in these DEX-pre-treated tissues, the mean ±SE $T_{max}$ and $pD_{50}$ values amounted to 102.9±13.1 g/g ASM weight and 4.89±0.05 –logM, respectively, and the latter determinations were similar to those obtained in control ASM. In contrast, pretreatment with DEX had no effect on the constrictor responses to ACh in control tissues (FIG. 7; open squares).

Figure 8:
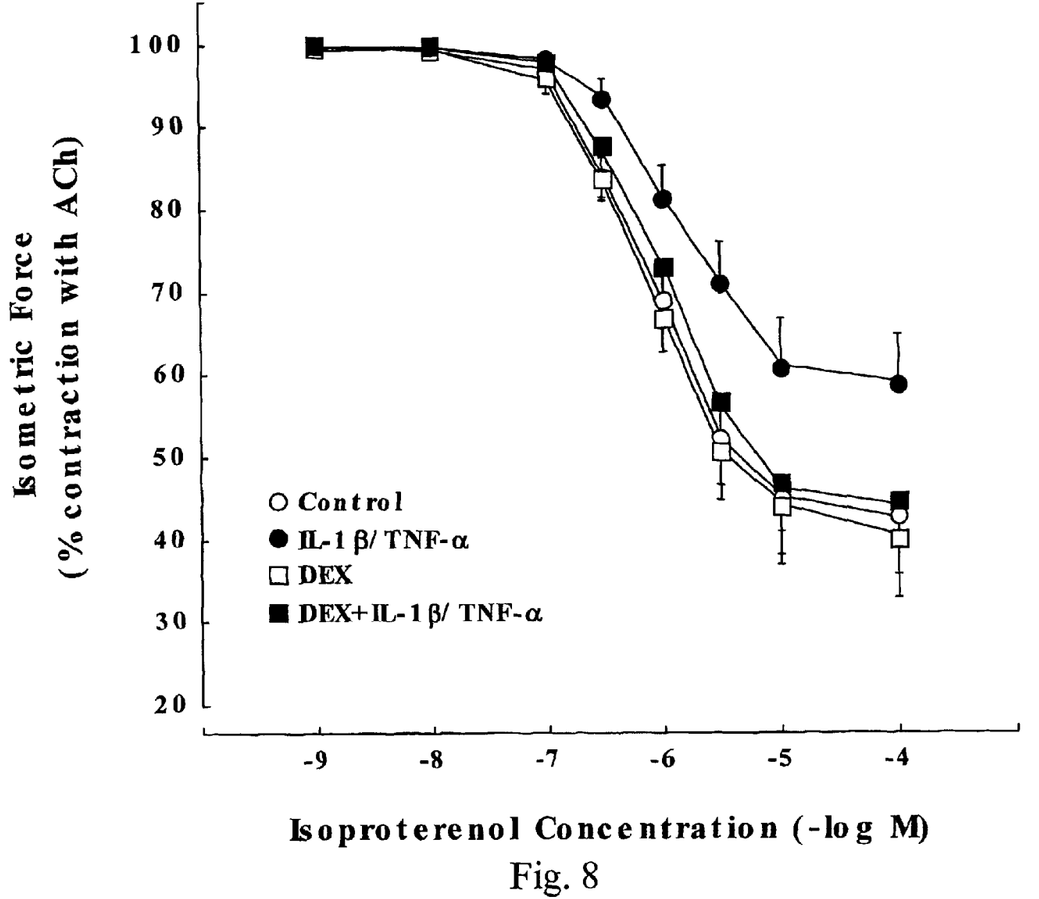
FIG. 8 is a graphical comparison of ASM relaxant responses to isoproterenol in control (open circles) and IL-1β/TNFα treated ASM tissues in the absence (filled circles) and presence (filled squares) of pretreatment with dexamethasone $10^{-5}$M. Data represent means ±SE from six paired experiments. Relative to tissues incubated with media alone, both the $R_{max}$ and $pD_{50}$ responses to isoproterenol were significantly enhanced in ASM segments that were exposed to IL-1β/TNFα, whereas the latter effects on the $R_{max}$ and $pD_{50}$ values were largely prevented by pre-treating the ASM tissues with dexamethasone (p≦0.01 and p≦0.05, respectively). In contrast, treatment with dexamethasone $10^{-5}$M alone (open squares), had no effects on either the $R_{max}$ or $pD_{50}$ responses to isoproterenol.

Comparable to the above protective effects of DEX on cytokine-induced changes in ASM constrictor responsiveness, the impaired beta-adrenoceptor-mediated relaxation responses to isoproterenol obtained in IL-1β/TNFα exposed ASM were also completely abrogated by pre-treating the tissues with DEX (FIG. 8). Accordingly, in these DEX-pre-treated tissues, the mean $R_{max}$ and $pD_{50}$ values for isoproterenol averaged 55.5±5.7% and 5.99±0.06 –logM, respectively; and the latter determinations were similar to those obtained in control ASM. In contrast, pretreatment with DEX had no effect on the relaxation responses to isoproterenol in control tissues (FIG. 8; open squares).

Figure 9:
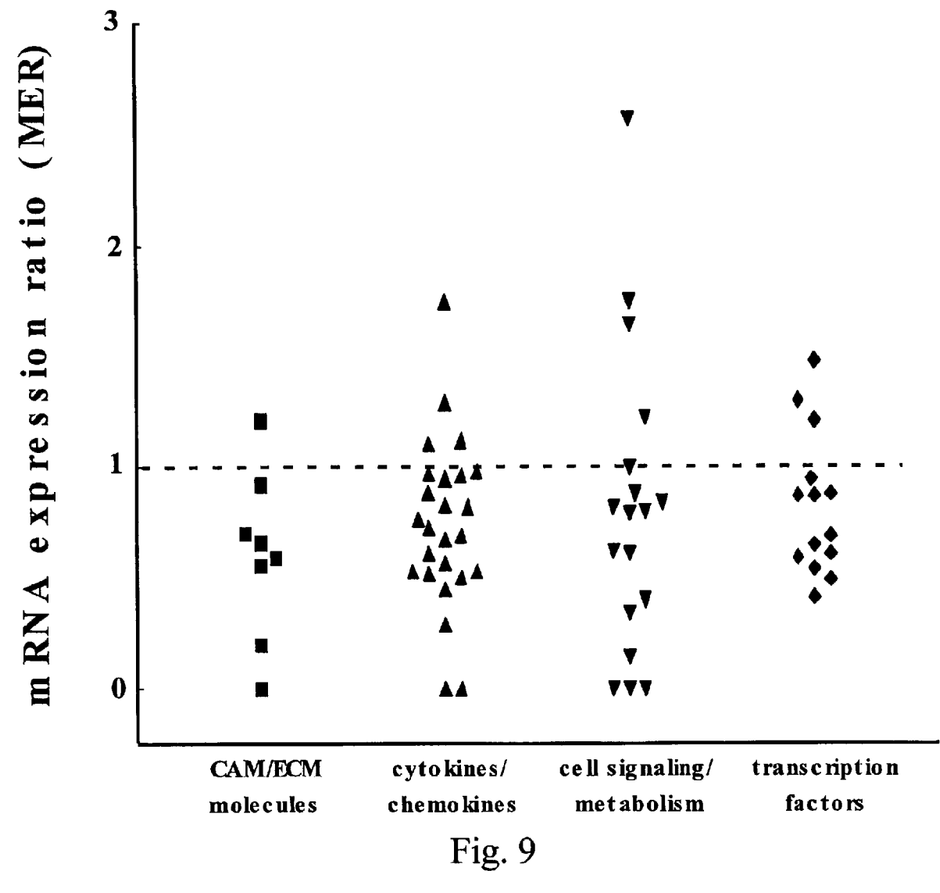
FIG. 9 is a graph showing the effects of dexamethasone on IL-1β/TNFα induced gene expression in human ASM cells, using a human DNA gene chip from Affymetrix. All genes belonging to the four categories of genes shown in FIGS. 3-6 are illustrated. Data represent dexamethasone-mediated mean inhibition (MER=1.0) and mean enhancement (MER >1.0) of mRNA expression from maximum levels induced by IL-1β/TNFα treatment from 2 separate experiments.

Description of the Effects of Gglucocorticoids on IL-1β/TNFα Induced Gene Expression in ASM Cells Given the efficacy of DEX in ablating the effects of IL-1β/TNFα on ASM responsiveness, the ability of DEX to modulate the above observed effects of IL-1β/TNFα on multiple gene expression in ASM cells was examined. Paired cultures of ASM cells were exposed to media alone (control) or to IL-1β/TNFα in the absence and presence of DEX ($10^{-5}$M), with each condition examined in duplicate. For any given gene, sensitivity to DEX was then determined as the ratio of the altered mRNA levels elicited by IL-1β/TNFα in the presence/absence of DEX. Accordingly, a mRNA expression ratio (MER) of 1.0 implies a lack of effect of DEX, whereas MER values below and above 1.0 denote DEX-induced repression and stimulation of mRNA expression, respectively. The results demonstrate that the upregulated mRNA levels exhibited by cells exposed to IL-1β/TNFα were largely repressed by pre-treating the cells with DEX, as evidenced by MER values below 1.0 for the majority of genes belonging to each category (FIG. 9). Not all genes, however, displayed DEX sensitivity and, as further shown in FIG. 9, a small number of genes in each category exhibited stimulation of IL-1β/TNFα induced mRNA expression in the presence of DEX (i.e., MER >1.0). in evaluating the variability in DEX sensitivity within each category of genes, no correlation was found between MER values of the different genes and the corresponding magnitudes of IL-1β/TNFα induced enhanced mRNA expression in the absence of DEX.

The DEX-sensitive genes depicted in FIG. 9 that exhibit ≧10% DEX-induced decrease in mRNA expression (i.e., MER ≦0.90) are identified in Table 1. It will be noted that a strong repressive effect of DEX was seen for genes known to be involved in the regulation of cAMP and $Ca^{2+}$ mobilization, including the phosphodiesterase D4 and plasma membrane $Ca^{2+}$ ATPase genes, which provided MER values of 0.40 and 0.34, respectively, corresponding to 60% and 66% inhibition of IL-1β/TNFα induced mRNA expression in the presence of DEX, respectively. Additionally, certain cytokine/chemokine-related and other cell signaling-related genes were significantly inhibited by DEX, including the pro-IL-1β, L-8, IL-13R, small inducible cytokine subfamily (SCY)-B2, -B6, -A7, and bradykinin receptor-2 (BKR2) genes. Moreover, it is relevant to note that the p50-NF-kB gene, which belongs to the NF-kB family of inducible transcription factors that regulates the host immune and inflammatory responses, was inhibited by 51% by DEX (i.e., MER=0.49). Finally, MMP3, MMp10 and MMp12, genes which are importantly implicated in tissue remodeling, were also markedly inhibited by DEX.

TABLE 1

Genes repressed by DEX in IL-1β/TNFα treated ASM cells

| Gene Category | Name/GenBank | MER |
|---|---|---|
| CAM/ECM Molecules | | |
| Intercellular adhesion molecule-1 | ICAM-1/M24283 | 0.66 |
| Matrix metalloproteinase-3 | MMP3/X05232 | 0.70 |
| Matrix metalloproteinase-10 | MMP10/X07820 | 0.00 |
| Matrix metalloproteinase-12 | MMP12/L23808 | 0.20 |
| Ninjurin-1 | NINJ1/U72661 | 0.59 |
| CD83 | CD83/Z11697 | 0.56 |
| Cytokines/Chemokines | | |
| pro-Interleukin-1β | IL-1β/X04500 | 0.45 |
| Small inducible cytokine subfamily B3 | SCYB3/X53800 | 0.83 |
| Colony Stimulating factor-2 | CSF2/M13207 | 0.53 |
| RANTES | RANTES/M21121 | 0.67 |
| Interleukin-6 | IL-6/X04602 | 0.89 |
| Fibroblast growth factor-2 | FGF2/J04513 | 0.69 |
| Interleukin-8 | IL-8/M28130 | 0.57 |
| Small inducible cytokine subfamily B2 | SCYB2/M57731 | 0.52 |
| Inhibin | INHBA/X57579 | 0.00 |
| Interleukin-13 receptor-α | IL-1 RA2/U70981 | 0.00 |
| Small inducible cytokine subfamily B6 | SCYB6/U83303 | 0.61 |
| Small inducible cytokine subfamily A7 | SCYA7/X72308 | 0.50 |
| Monocyte-derived chemotactic protein | MDCP/HG4069 | 0.29 |
| Pre-B cell colony-enhancing factor | PBEF/U02020 | 0.73 |
| Cell Signaling/Metabolism | | |
| Phosphodiesterase-4B | PDE4B/L20971 | 0.40 |
| Adenosine monophosphate deaminase | AMPD3/D12775 | 0.82 |
| Urokinase plasminogen activator | uPA/X02419 | 0.00 |
| Bradykinin receptor-2 | BKR2/X86163 | 0.62 |
| CDC28 protein kinase-2 | CKS2/X54942 | 0.80 |
| Plasma membrane $Ca^{2+}$ ATPase | ATP2B1/J04027 | 0.34 |
| Superoxide dismutase-2 | SOD2/X07834 | 0.89 |
| Transcription Factors | | |
| Nuclear factor of kappa light polypeptide | NFKB1/M58603 | 0.87 |
| Nuclear factor of activated T cells-C1 | NFATC1/U08015 | 0.61 |
| BCL2-related protein A1 | BCL2A1/U29680 | 0.41 |
| Signal transducer/activator of transcription 5 | STAT5A/U43185 | 0.87 |
| Nef-associated factor 1 | NAF1/D30755 | 0.88 |
| Nuclear receptor subfamily 4 | NR4A3/U12767 | 0.54 |
| Putative lymphocyte G0/G1 switch gene | G0S2/M72885 | 0.65 |
| p50-NF-KB | p50-NF-kB/S76638 | 0.49 |
| PTX3 promoter | PTX3/X97748 | 0.69 |

Table 1. Genes repressed by dexamethasone (DEX) in IL-1β/TNFα treated human ASM cells. Genes are identified by their gene symbols and GenBank accession numbers. The MER value given for each gene refers to the ratio of mRNA expression levels elicited by IL-1β/TNFα in the presence versus absence of DEX.

Among the collection of DEX-sensitive genes exhibiting MER values ≧1.10, as shown in Table 2, those belonging the cell signaling-related category included 11-beta-hydroxysteroid-dehydroxygenase-1, the MAP kinase subtype, MAPKKK5, and the ATP-binding cassette gene, ABC-B2. In the cytokine/chemokine-related category, DEX-induced augmented mRNA expression was most evidenced by genes encoding epithelial-derived neutrophil-activating peptide 78 (SCYB5), colony (granulocyte) stimulating factor 3 (CSF3), TNFα induced protein 3 (TNFα-IP3)

and TNFα-IP6. Other genes upregulated by DEX include the transcription factor-related gene, CCAAT-enhancer binding protein (C-EBP)-delta, and the CAM/ECM molecule-related gene, tenascin C.

TABLE 2

Genes stimulated by DEX in IL-1β/TNFα treated ASM cells

| Gene Category | Name/GenBank | MER |
|---|---|---|
| CAM/ECM Molecules | | |
| Tenascin C | HXB/X78565 | 1.21 |
| Cytokines/Chemokines | | |
| Small inducible subfamily B5 | SCYB5/L37036 | 1.75 |
| Tumor necrosis factor-α-induced protein 6 | TNF-αIP6/M31165 | 1.11 |
| Tumor necrosis factor-α-induced protein 3 | TNF-αIP3/M59465 | 1.21 |
| Small inducible cytokine subfamily B10 | SCYB10/X02530 | 1.12 |
| Colony stimulating factor-3 | CSF-3/X03656 | 1.31 |
| Cell Signaling/Metabolism | | |
| Guanylate binding protein-1 | GBP1/M55542 | 1.22 |
| Hydroxysteroid (11-β) dehydrogenase-1 | HSD11B1/M7665 | 2.57 |
| ATP-binding cassette | ABCB2/X57522 | 1.75 |
| Mitogen-activated protein kinase kinase kinase-5 | MAP3K5/U67156 | 1.65 |
| Transcription Factors | | |
| KIAA0247 gene product | KIAA0247/D87434 | 1.3 |
| Enhancer binding protein | CEBPD/M83667 | 1.48 |

Table 2. Genes stimulated by DEX in IL-1β/TNFα treated ASM cells. Genes are identified by their gene symbol and GenBank accession numbers. The MER value given for each gene refers to the ratio of mRNA expression levels elicited by IL-1β/TNFα in the presence or absence of DEX.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying an inhibitor of an inflammatory disease, comprising:
   a) assaying the expression level of one or more informative genes that are differentially expressed in the presence or absence of IL-1β and TNFα in one or more resident tissue cells induced to mimic the inflammatory disease, and in one or more resident tissue cells that have not been induced to mimic the inflammatory disease, thereby producing an expression profile for the induced resident tissue cells and for the uninduced resident tissue cells;
   b) assaying the expression level of the one or more informative genes in (a) in one or more resident tissue cells in the presence of IL-1β and TNFα and in the presence of a potential inhibitor of the inflammatory disease, thereby producing an expression profile for the induced resident tissue cells in the presence of the inhibitor, and
   c) comparing the expression profile (b) in the induced resident tissue cells in the presence of the inhibitor with the expression profiles of (a),
   wherein if the expression of one or more informative genes in the expression profile in (b) is more comparable to the expression of the one or more informative genes in the expression profile of the uninduced resident tissue cells than that of the induced resident tissue cells, then the inhibitor is an inhibitor of an inflammatory disease.

2. The method of claim 1, wherein the resident tissue cells are selected from the group consisting of: airway smooth muscle cells, epithelial cells, keratinocytes, synovial cells, glial cells and villous intestinal cells.

3. The method of claim 2, wherein the resident tissue cells are airway smooth muscle or airway epithelial cells.

4. The method of claim 1, wherein the inflammatory disease is selected from the group consisting of: asthma, atopy, rheumatoid arthritis, psoriasis, inflammatory bowel disease and chronic obstructive pulmonary disease.

* * * * *